United States Patent [19]
Pinsl-Ober et al.

[11] Patent Number: 5,424,212
[45] Date of Patent: Jun. 13, 1995

[54] ANALYSIS SYSTEM FOR THE AUTOMATIC ANALYSIS OF BODY FLUIDS

[75] Inventors: Judith Pinsl-Ober, Tutzing; Herbert Buschek; Klaus Erler, both of Weilheim, all of Germany

[73] Assignee: Boehringer Mannheim GmbH, Mannheim, Germany

[21] Appl. No.: 197,457

[22] Filed: Feb. 16, 1994

Related U.S. Application Data

[63] Continuation of Ser. No. 902,253, Jun. 22, 1992, abandoned.

[30] Foreign Application Priority Data

Jun. 26, 1991 [DE] Germany .................. 41 21 089.1

[51] Int. Cl.⁶ .................. G01N 21/13; G01N 33/48
[52] U.S. Cl. .................. 436/50; 422/64; 422/67; 436/43
[58] Field of Search .......... 422/63, 64, 65, 66, 422/67; 436/8, 43, 45, 50

[56] References Cited

U.S. PATENT DOCUMENTS

| | | | |
|---|---|---|---|
| 4,043,756 | 8/1977 | Sommervold | 23/230 |
| 4,080,833 | 3/1978 | Huber | 73/423 |
| 4,451,433 | 5/1984 | Yamashita et al. | 422/63 |
| 4,678,752 | 7/1987 | Thorne et al. | 435/291 |
| 4,678,755 | 7/1987 | Shinohara et al. | 436/43 |
| 4,774,055 | 9/1988 | Wakatake et al. | 422/64 |
| 4,781,891 | 11/1988 | Galle et al. | 422/64 |
| 4,900,513 | 2/1990 | Barker et al. | 422/64 |
| 4,933,146 | 6/1990 | Meyer et al. | 422/63 |
| 4,969,993 | 11/1990 | Nash, Jr. et al. | 210/198.2 |
| 5,032,362 | 7/1991 | Marsoner et al. | 422/81 |
| 5,075,077 | 12/1991 | Durley, III et al. | 422/56 |
| 5,147,610 | 9/1992 | Watanabe et al. | 422/64 |
| 5,229,074 | 7/1993 | Heath et al. | 422/64 |

FOREIGN PATENT DOCUMENTS

| | | |
|---|---|---|
| 0296259 | 12/1988 | European Pat. Off. . |
| 3102754 | 12/1981 | Germany . |
| 3717907 | 12/1987 | Germany . |
| 3839080 | 6/1989 | Germany . |

OTHER PUBLICATIONS

Japanese Patent No. 62-144071 (in German), Jun. 27, 1987.
Patent Abstracts of Japan, vol. 13, No. 239, Jun. 1989.
Patent Abstracts of Japan, vol. 12, No. 203, Jun. 1988.
Patent Abstracts of Japan, vol. 11, No. 373, Dec. 1987.
Patent Abstracts of Japan, vol. 12, No. 408, Oct. 1988.

*Primary Examiner*—Robert J. Warden
*Assistant Examiner*—Robert Carpenter
*Attorney, Agent, or Firm*—Nikaido, Marmelstein, Murray & Oram

[57] ABSTRACT

Analysis system for the automatic analysis of body fluids for a plurality of different analytes (parameters). An analytical apparatus incorporates reaction vessels (8) which are transported on the apparatus to various handling stations (10 to 16). The system also includes liquid reagents, which are held in readiness on the apparatus in reagent vessels (9), their volume sufficing for a large number of analyses. In order to achieve a high degree of analytical accuracy with reduced probability of operating errors and without significant increasing of the overall system costs, a calibrator is stored ready for use in liquid form in a calibrator station (17) of the analytical apparatus, the calibration is initiated and carried out fully automatically (i.e. without human intervention) for the various parameters independently of one another. For the initiation of the calibration for a parameter, in at least one system-immanent calibration-influencing variable is determined and combined logically with a control value defined specifically for the respective parameter and the decision on the initiation of the calibration is taken automatically in accordance with the logic combination.

21 Claims, 3 Drawing Sheets

ANALYSIS SYSTEM FOR THE AUTOMATIC ANALYSIS OF BODY FLUIDS

This application is a continuation of application Ser. No. 07/902,253 filed Jun. 22, 1992.

The invention relates to an analysis system for the automatic analysis of body fluids. The system is used for the quantitative determination of a plurality of different analytes (parameters). Components of the system are an analytical apparatus, reaction vessels, which are transported on the apparatus to various handling stations, liquid reagents, which are held in readiness in the apparatus in reagent vessels and the volume of which suffices for a large number of analyses, together with at least one liquid calibrator which contains at least one analyte in a known concentration. In addition the system may include further components, such as for example special sample vessels or control solutions.

The analysis systems to which the invention relates are frequently described as automatic wet-chemical selective multi-parameter analysis units. In these systems, individual reaction vessels are transported past various handling stations, the transport means used being in many cases a rotor rotatable in steps. The handling stations incorporate pipetting stations, in order to feed the samples and reagents into the reaction vessels in a defined amount, in many cases a mixing unit for blending purposes, and finally a measuring unit, in order to determine on completion of the analytical reaction a physically detectable measuring quantity from the reaction solution contained in the reaction vessels. In most cases the optical absorption in transmission is measured.

The automatic wet-chemical analysis units differ through said construction elements from the likewise widely distributed analysis systems in which there is used for each individual analysis an analysis element which contains the reagents required for the individual analyses in a package unit (usually in dry form). The package unit may take quite different forms, for example as test strips, so-called analysis chips, or as a "test pack". Such analysis systems will be referred to overall as test pack analysis systems.

The main advantage of automatic wet-chemical analysis units is the low analysis cost, because the reagents do not have to be packed individually in extremely small units. On the other hand it is far more difficult than with test pack systems to meet the constantly increasing requirements with regard to ease of operation, security against operating faults and low time requirement in respect of the operating personnel.

The present invention is directed particularly towards the calibration of automatic wet-chemical analysis units. Because of instabilities both of the reagents and of the apparatus it is necessary to carry out a calibration of the system from time to time by means of a calibrator, i.e. a liquid which contains the respective analyte (parameter) in a known concentration. With it an evaluation curve (functional connection between the physical measuring quantity, e.g. absorption, and the desired concentration) is plotted and stored in the apparatus. Since the evaluation curve usually is a straight line in the case of tests which are based on a photometric transmission measurement, there usually suffices for the calibration, in addition to the measurement of a blank reading, a measurement from a single calibrator with a concentration not equal to zero. In certain circumstances (where the calibration curve is a non-linear curve) several calibrations in different concentration ranges of a parameter are required.

The following calibration methods are mainly used:

a) The calibrator is introduced by an operator into the system and the calibration is requested for the desired parameter by manual input. The operator here determines the timing of each calibration in accordance with instructions from the reagent or apparatus manufacturers.

b) In the analytical apparatus time intervals (calibration intervals) are stored. After the expiry of each such interval the operating personnel are required to initiate a calibration manually. A variant of said system, under which a separate calibration interval is stored for each parameter, is described in U.S. Pat. No. 4,678,755. The necessity for a calibration is here displayed for the user in a variety of ways (for example as a table on a screen) and in addition an acoustic alarm may also be triggered in order to indicate the need for a calibration.

In the Japanese patent application with the publication number 62-144071 there is described the possibility of measuring at particular periodic intervals, as a supplement to the conventionally performed calibration, the absorbance of a zero standard (blank), in order thereby to allow for time-dependent variations of the reagent. An important example of a parameter with which such a periodic adjustment of the zero value is advantageous is the analysis of bicarbonate, which is based on the detection of $CO_2$. It is characteristic of said test that the properties of the reagent vary relatively rapidly due to the unavoidable take-up of $CO_2$ from the air. It is therefore necessary to adjust the zero value of the calibration at regular intervals. This takes place by means of a measurement on a physiological saline salt solution as blank. Said solution, in contrast to customary calibrators with a concentration not equal to zero, is extremely stable in storage.

Although the above-mentioned publication deals with a calibration, said method is concerned only with an adjustment of the evaluation curve plotted originally in the conventional manner (using a calibrator with a concentration not equal to zero) to the time-dependent variation of the reagent, the evaluation curve being displaced in each case in accordance with the measured zero value. The method is not necessarily applicable to other barameters. In practice it is used exclusively for adjusting the zero value in bicarbonate determinations. The rigid periodical carrying out of the adjustment measurement at constant intervals is not suitable for a fully automatic calibration.

In order to achieve, in the case of a wet-chemical analysis system of the kind described, a high degree of analytical accuracy with a reduced probability of operating errors and without increasing significantly the overall costs of the system, it is proposed according to the invention that at the outset the calibrator be stored in a calibrator station of the analytical apparatus in liquid form ready for use (i.e. so that it may without human intervention be withdrawn from the calibrator vessel and analyzed) and the calibration be started (initiated) and performed automatically (i.e. without an operator having to intervene) for various parameters independently of one another. A specifically predetermined calibration initiation cycle, takes place for the initiation of the calibration for a parameter in which at least one system-immanent calibration-influencing variable is interrogated in each case and combined logically with a control value defined specifically for the respective parameter. The decision on the initiation of the calibration is taken in accordance with the result of the logical combination. The calibration initiation cycle is advisably carried out successively for all the analysis parameters for which the apparatus is set up. The process is repeated continuously or at particular intervals of time.

The invention permits the carrying out of the required calibrations without human intervention. Errors are thereby avoided. The initiation of the calibration is adapted specifically to the parameter in each case and in addition system-immanent calibration-influencing variables are allowed for within the scope of the calibration initiation cycle. As a result, on the one hand, longer time intervals between the calibrations for a particular parameter are made possible in many cases and hence savings in time and costs achieved. On the other, disturbance factors which make premature re-calibration necessary may be automatically recognized. Considerable progress is achieved with respect to the aim, long striven for in the chemical analysis field, of obtaining wet chemical analysis systems which work operator-independently ("stand-alone operation").

The invention overcomes the view prevalent in professional circles that analytical reliability requires that each calibration step be initiated individually and be carried out with a freshly prepared calibrator.

A characteristic feature of the invention is that the initiation of a calibration takes place on the basis of a defined algorithm, which is designated as the calibration initiation cycle. Said algorithm is, as will be explained in detail below, adapted specifically to the parameter in each case. This relates to the selection of one or more system-immanent influencing variables which are taken into account at the initiation of the calibration of a particular parameter. It also relates to the determination of the respective defined control value and the nature of the logical combination.

System-immanent calibration-influencing variables (which may also be termed as calibration indicators) are for the purpose of the invention states or properties of components of the analytical system, including the samples, which are of importance with regard to the need to initiate a calibration. In the context of the invention variables were found (which bear no direct relationship to the nature of the calibrator, its nominal concentration value or its measured concentration value (actual value)), by monitoring which the need for a calibration during the operation of a diagnostic analysis system is recognized automatically, so that the initiation of the calibration at the correct moment in time is possible. Said system-immanent influencing variables are suited to characterising the state of the overall system, consisting of samples, calibrators, control solutions, reagents and analytical apparatus to the extent required for the initiation of the particular calibration. By monitoring them, the cause which makes calibration necessary for a parameter (or is suited to postponing a calibration) may be recognized automatically. The system is therefore suitable for self-diagnosis and also—since the calibration is carried out automatically—for self-regulation.

A system-immanent calibration-influencing variable may be a measured value (for example the absorption or the pH value of a reagent). In this case the control value with which the detected measured value is combined is a numerical value. It is also possible however for this value to be an information item concerning a system component (for example the reagent batch and the bottle number of the reagent), which is notified to the system in machine-readable form.

Finally, there must also be regarded as system-immanent calibration-influencing variables information items which are usually present in any case in an analytical apparatus, but which in the context of the invention are used in a novel way for the automatic initiation of a calibration. Examples of these are the nature of the samples (in particular serum or urine) for which analyses are to be conducted within an automatic analysis operation (run) of the apparatus, as well as the analyses (parameters) requested for the individual samples and the sequence, usually calculated from the latter by the computer of the apparatus, in which the requests are processed. In this case there may be input as a control value for example a limit numerical value of analyses which may still be carried out for a particular parameter at the end of a run without a calibration being necessary. The nature of the sample (serum or urine) may logically be combined with a stored information item indicating whether a calibration for said sample type and the parameter requested in conjunction with the latter has already taken place. These various possibilities for taking account of system-immanent influencing variables will be explained in greater detail below.

It becomes clear that the control value may be both a logical value describing a state and also a numerical value. In general it is a value which is suited to the control of the calibration initiation cycle by logical combination with a system-immanent influencing variable. If the system-immanent influencing variable is a continuously changing variable, such as for example the absorption value of the reagent, the control value is usually a threshold value or a range of values of said variables. If the calibration-influencing variable has only two logical states, such as for example during the interrogation of a reagent bottle switching (no new bottle corresponds logically to 0, new bottle corresponds logically to 1), the control value normally has likewise only two logical states (e.g. logic 0 for "no calibration at bottle switching" and logic 1 for "calibration at bottle switching").

Since the need for a new calibration of a particular parameter depends essentially on time-dependent changes in the reagents used, the initiation of a calibration usually also takes place mainly as a function of time, a calibration interval being stored for each parameter. According to the invention there takes place in addition however a "system feedback", in which further influencing variables are used by means of logical combination.

A further enhancing of the reliability and analytical security is achieved by the following preferred measures.

After each calibration of a parameter a control measurement of the same parameter should be carried out with a control solution of a known concentration. This enables errors to be detected during the calibration measurement, for example due to an air bubble in the photometer. The control solution may in principle be the same calibrator with which the calibration was carried out. Preferably, however, a special control solution is used, which is stored ready for use in a control solution station of the apparatus. In this way calibration errors which have their cause in the calibrator are also detected.

The calibrator station and where applicable the control solution station (which are with advantage combined physically) are cooled. In this way errors due to evaporation and/or chemical decomposition of the calibrator or the control solution are reduced. Although the cooling requires a considerable technical outlay, the latter is more than offset by the advantages of the invention.

In order to make possible the calibration automatically during a whole operating day, the calibrator should be in the liquid state and "day-stable" in contact with air, i.e. the concentration of the respective analyte should remain in the target value range during a full working day.

BRIEF DESCRIPTION OF THE DRAWINGS

The invention will be explained in detail below with reference to an exemplifying embodiment shown diagrammatically in the figures, where.

Figure 1:
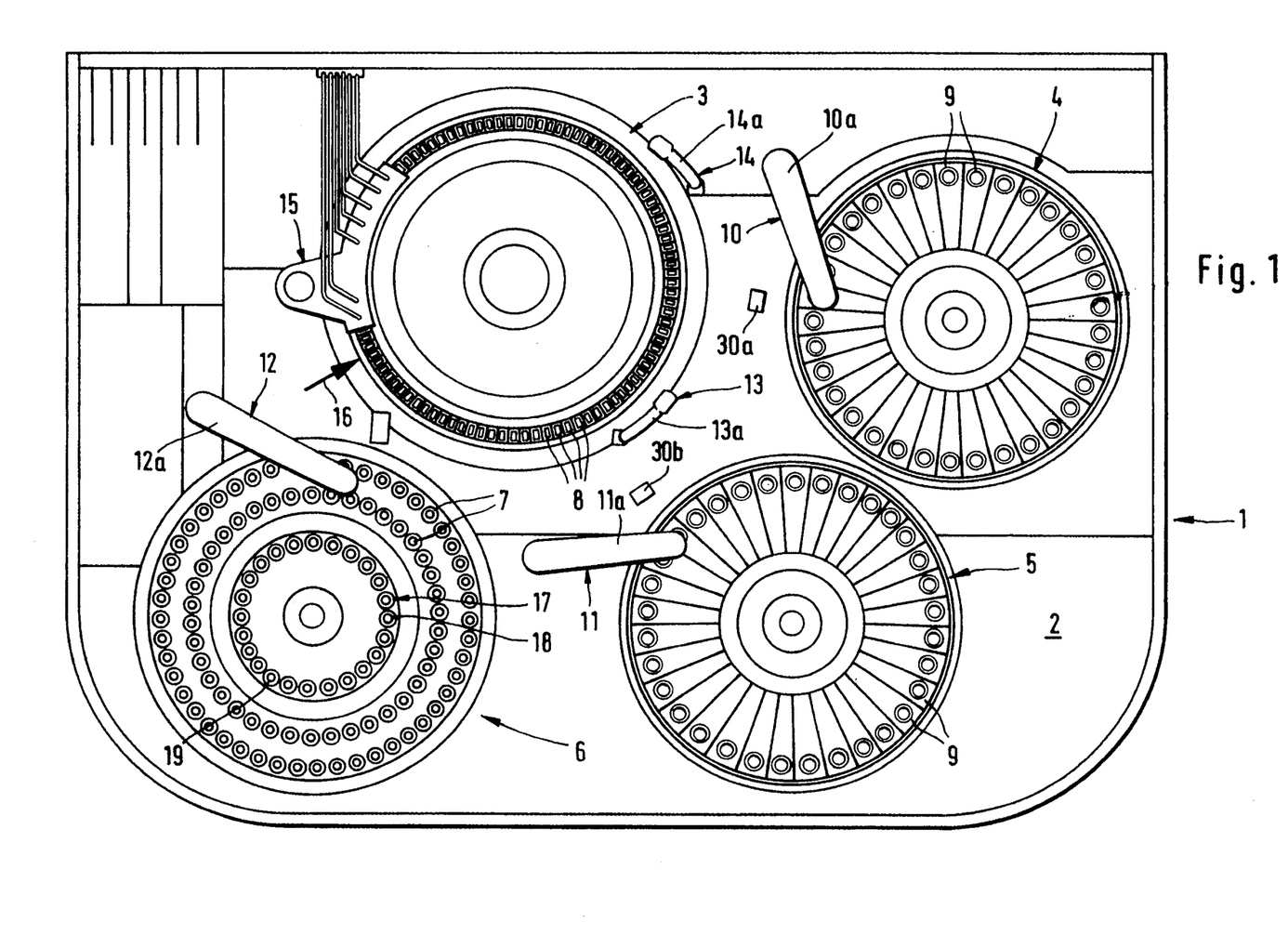
FIG. 1 shows a top view of an analytical apparatus suitable for the invention, FIG. 2 a block diagram of an analytical apparatus suitable for the invention, FIG. 3 a perspective overall view of a reagent vessel detector, FIG. 4 a perspective overall view of a calibrator vessel detector, FIG. 5 a sequence diagram illustrating the operating sequence in an analysis system according to the invention.

The analysis system 1 illustrated in FIG. 1 shows on a handling table 2 a reaction rotor 3, two reagent rotors 4 and 5 with reagent vessels 9 and a sample rotor 6 with sample vessels 7. On the reaction rotor 3 there are arranged in a circle numerous reaction vessels 8. At the periphery of the reaction rotor 3 are located various handling stations, namely pipetting stations 10, 11, 12, mixing stations 13, 14 and a washing station 15 for cleaning the reaction vessels 8. The swivel arms 10a to 14a of the various stations are computer-controlled and are used to transfer the sample and the reagents respectively into the reaction vessels 8 at the correct time, or to dip an agitator paddle of the mixing stations 13, 14 into the reaction vessels 8 for the mixing. The photometric measurement takes place, in the case of the apparatus shown, right through the reaction vessels, which are constructed in their lower part as optical cuvettes. The photometry station is therefore located beneath the covering of the handling table 2 and is symbolized by an arrow 16.

The layout of the system is so far conventional and does not have to be explained further.

A special feature of the system according to the invention is the calibrator station 17, which in the case shown is incorporated in the sample rotor 6. It contains a plurality of calibrators, which are stored ready for use in liquid form in calibrator vessels 18. The number of calibrators required depends on the number of parameters and on the possibility of using multi-parameter calibrators with which a plurality of different analytes in known concentration are contained in a single solution. In order to ensure the required day stability, it is in the context of the invention frequently advantageous to use single-type calibrators. Since operation takes place automatically, practically no additional outlay is involved in the latter.

The calibrator station 17 contains in the preferred case shown additional control vessels 19, which contain control solutions. The calibrator station 17 should be cooled as a whole (for example by means of Peltier elements). The openings in the calibrator vessels 18 and in the control vessels 19 are located within the range of the pipetting needles swivellable on the arm 12a of the sample pipetting station 12 and may thus be transferred instead of a sample into a reaction vessel 8 on the reaction reactor 3.

Both the liquid calibrators stored in the calibrator vessels 18 and the control solutions stored in the control vessels 19 contain the respective analytes in known concentrations. A calibrator and a control solution for a particular parameter may be identical in certain circumstances. Use is however often made as calibrators of solutions in which the concentration of the respective analyte lies in a very narrow target value range and the analyte is dissolved in a solvent which ensures a high stability of the calibrator. In the case of a control solution, however, the solvent used is preferably serum or a serum-type liquid and the target value range of the analyte is somewhat broader.

In order to carry out a calibration, the rotor 6—without human intervention being required—is rotated in each case into a position in which the required calibrator is located in the swivelling range of the arm 12a of the sample pipetting station 12. A measured partial amount of the calibrator is withdrawn from the calibrator vessel 18 and transferred into the reaction vessel 8. There reagents are added in the usual manner and the colour change resulting from the reaction is determined photometrically. Said measured value is defined in the computer of the apparatus as a new calibration factor and used in the same manner as with manually initiated calibrations for the correction of the evaluation curve.

Figure 2:
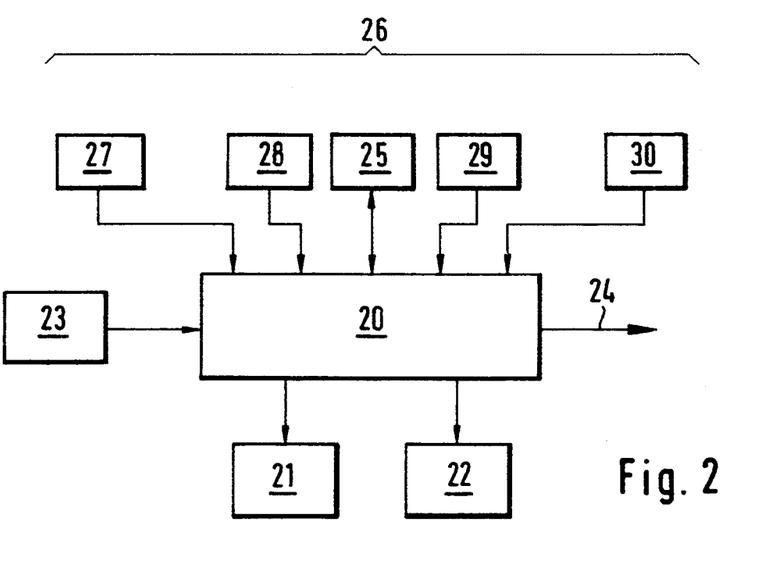

FIG. 2 illustrates the interaction of the various components (shown in the form of a block diagram) of a system according to the invention. A microprocessor-controlled central processing unit 20 with storage means 25 is used in the usual manner to activate a rotor control unit 21 and a handling station control unit 22, in order to control the required rotational movements of the rotors 3, 4, 5 and 6 and the movement, suction, ejection, washing and measuring operations of the handling stations 10 to 16. The measured values of the photometry station 16 are supplied via a measured value interface 23 to the central processing unit 20, processed and output via a data output 24 to data output units (not shown), such as for example a printer or a screen.

It is crucial to the invention that means, designated overall as 26, are provided for taking account of various system-immanent influencing variables, the value of which influences the initiation of a calibration. A reagent vessel detector 27 is shown, together with a reagent filling level detector 28, a reagent absorption detector 29, a reagent pH detector 30 and the storage means 25.

The individual detectors may be of the conventional kind to a large extent. The term "detection" has a broad connotation here as any form of detection or observation of a system-immanent influencing variable.

Figure 3:
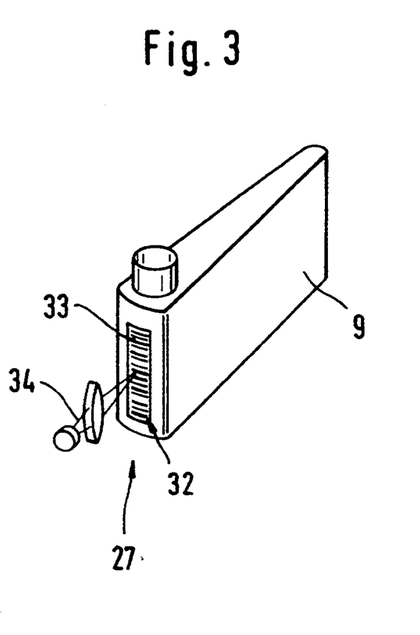

FIG. 3 shows a preferred form of a reagent vessel detector 27. The reagent vessel 9 bears on a label 32 a machine-readable coding in the form of a bar code 33. On the apparatus side a reflection code reader 34 is provided, which is constructed conventionally and represented merely symbolically in the figure.

The reflection code reader 34 is installed at the periphery of the respective reagent rotor 4, 5 in such a way that it can read the bar code on the reagent vessels 9 located in the apparatus. A reagent vessel detector 27 constructed in this way fulfils a dual function in the context of the invention. Firstly, it serves to recognize the switching of a reagent vessel. Secondly, it permits the bar code 33 to be read. The latter contains an information item on the batch of the reagent and preferably additionally on the identity of the reagent bottle (manufacturing number). The reading of said bar code may be utilized, in addition to the initiation of a calibration, also for complementary security measures. In particular it is checked whether the correct reagent is used (reagent identification). It may also be established whether the same bottle is introduced into the apparatus several times, which would indicate misuse of the reagent vessel to the detriment of analytical accuracy.

Figure 4:
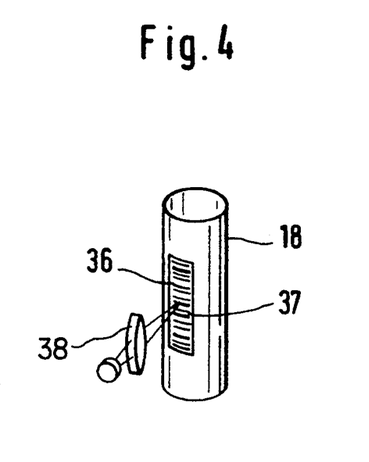

As is shown in FIG. 4, the calibrator vessels also preferably bear a label 36 with a bar code 37. A bar code reader 38, once again constructed in the conventional manner, serves for the detection of the coded information. The code 37 contains in particular information items on the parameter or parameters of the calibrator. A "positive calibrator identification" is thereby ensured, i.e. confusion of the calibrator is eliminated.

The detection of the reagent liquid level (filling level) in the reagent vessels 9 may take place by known methods, for example by means of a conductivity measurement or by means of a capacitance measurement. The measuring device is preferably located on the suction needle of the respective pipetting arm 10a, 11a, so that the height position of the respective pipettor on immersion into the reagent liquid is detected. A filling level detector of this kind is used in many known analysis systems in order to generate a warning signal if the stock of reagent in one of the vessels 9 falls below a minimum level.

There is preferably used as the reagent pH detector a standard pH electrode, which may be arranged on the reaction rotor 3 or else directly on the reagent rotor 4 or 5. In the case shown a pH detector is arranged under the table 2, whose filling openings 30a and 30b are in each case positioned within the swivelling range of the arms 10a, 11a of the reagent pipetting stations 10, 11, so that if necessary a sample of the reagent may be transferred into the respective filling opening 30a, 30b.

For the detection of the optical absorption of the reagent no additional construction means are required. There is used instead as a reagent absorption detector the photometry station 16, the pure reagent being subjected to photometry without the addition of any sample.

The storage means 25 of the central processing unit 20 must also be regarded as a means of taking account of system-immanent influencing variables if such variables are stored there. In particular, information items on the samples or analyses may be involved here, as will be explained in detail below.

As mentioned, the system feedback of the system-immanent influencing variables has in the form of a logical combination an influence on the initiation of a calibration. Examples will be explained with reference to FIG. 5.

Figure 5:
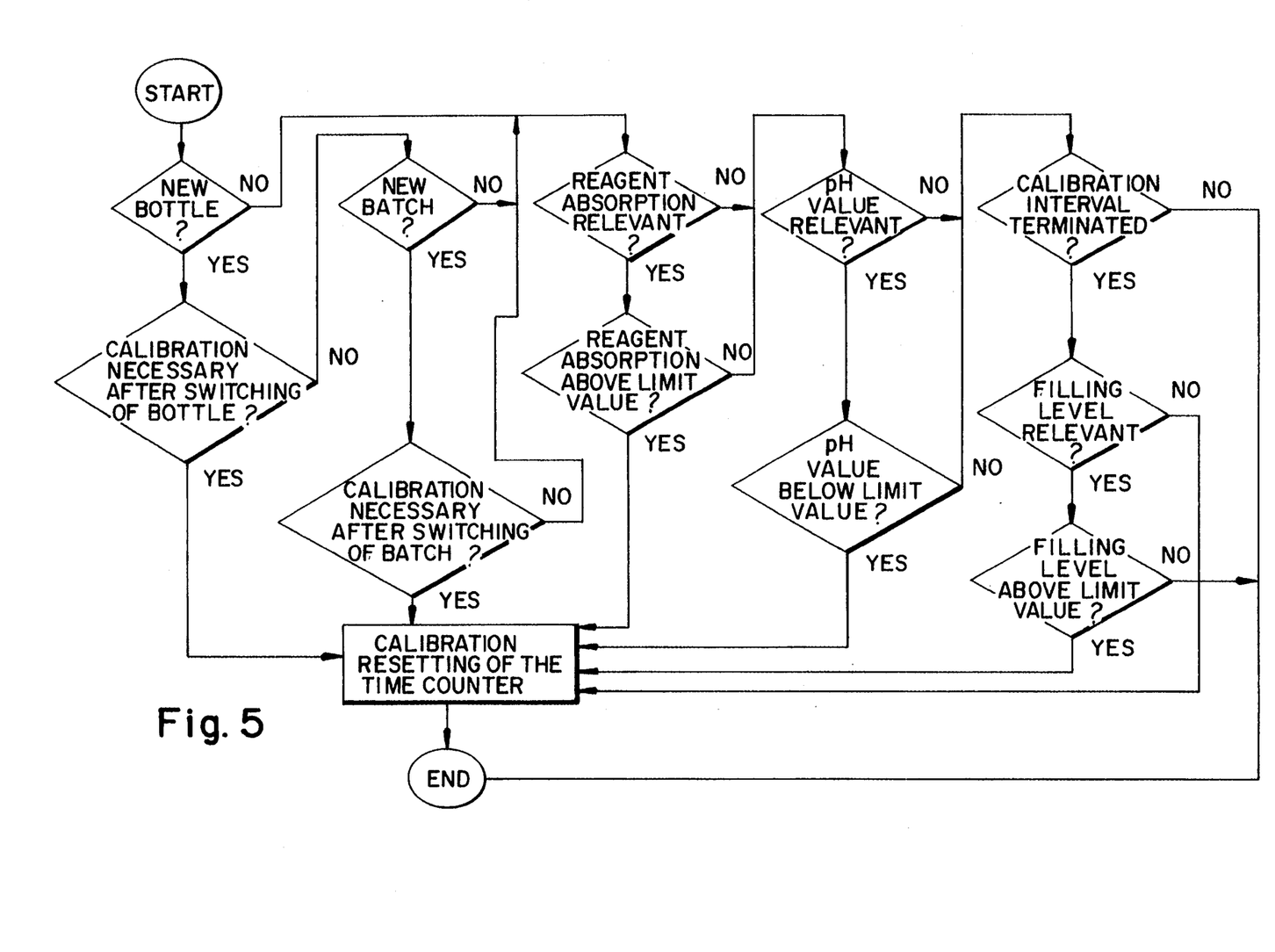

The sequence diagram of a calibration initiation cycle for a parameter is shown, in which in addition to a calibration interval the switching of the reagent vessel, the switching of the batch of the reagent, the filling level of the reagent, the pH value and the reagent absorption are taken into account as system-immanent influencing variables. The cycle shown runs automatically on the apparatus at stipulated intervals of time. Cycles of the same kind are performed individually in succession for the individual parameters.

Within the cycle there takes place first of all an interrogation whether a switching of the reagent vessel (bottle) has been effected (since the last calibration initiation cycle of the same parameter). This is indicated by the reagent vessel detector, the switching of the bottle leading to a change in state of a storage element (flip-flop), whose actual value is interrogated at this stage of the cycle.

If bottle switching has been effected, an interrogation takes place whether re-calibration is necessary on switching of the bottle. The answer is dependent on the respective reagent and hence on the parameter. Said answer is stored as a logic control value for each parameter at the setting up of the system. In the case of reagents with critical stability properties the answer "yes" is stored and a calibration takes place at each switching of the reagent bottle.

If the last-mentioned interrogation leads to the answer "no", corresponding interrogations take place regarding the switching of the batch and the necessity for re-calibration in the event of hatch switching. It is thereby taken into account that on the switching of a reagent bottle a new batch of the reagent is often used, and said batch switching may also make re-calibration necessary in cases where bottle switching with unchanged batch does not lead to the initiation of a calibration.

If one of said interrogations or the first interrogation (regarding switching of the bottle) leads to the answer "no", the interrogation whether the reagent absorption is relevant for the respective parameter takes place. This also has been stored for each parameter at the setting up of the system. If the answer is "yes", an interrogation takes place whether the reagent absorption lies above a limit value (which is parameter-specific and stored as a control value). A calibration takes place if the result is positive.

If the answer to one of the interrogations regarding the reagent absorption is "no", corresponding interrogations regarding the pH value take place. In this case a calibration takes place if the pH value lies below a limit value stored as control value.

If here also both interrogations are answered with a "no", there next takes place the interrogation whether the calibration interval has expired. The cycle is terminated if the answer is "no".

If the answer is "yes", two further interrogations take place regarding the filling level of the reagent in the respective reagent vessel. The aim of said interrogations is to avoid the outlay on calibrator liquid and machine time associated with the re-calibration if the filling level is below a defined level value (i.e. there is only a small amount of reagent still left in the reagent vessel) and a slight exceeding of the calibration interval may be tolerated for the parameter concerned. If either the filling level for the parameter concerned is not relevant (i.e. a calibration has to take place even with a low filling level) or the filling level lies above the limit value stored as control value, a calibration will be initiated. It will be dispensed with, however, if the filling level is relevant and lies below the limit value.

If a calibration is initiated, resetting of the counter which monitors the expiry of the calibration interval takes place in each case.

In the case of the examples shown in FIG. 5, system-immanent influencing variables are allowed for by means of logic combinations, in order on the one hand to trigger additional calibration operations (at bottle or batch switchings or on the attainment of the pH or absorption limit values) and on the other to avoid unnecessary calibration operations (with low filling level of the reagent). For the rest the calibration takes place at defined intervals of time after the expiry of a respective calibration interval.

Influencing variables which are linked directly to the state of the reagent may also be used completely independently of the time sequence for the initiation of a calibration operation. Influencing variables of this kind are the absorption of the reagent or its pH value. It has been found, in fact, that said values represent in certain circumstances a better indicator for the state of the reagent than the time of use.

Changes to reagents in automatic wet-chemical analysis units are dependent on a large number of influencing factors, for example the temperature, the air humidity, the age of the reagents prior to opening of the reagent container (i.e. the storage time) and so on. In order to allow for this, the determination of a calibration interval defined exclusively in terms of time must be based on "worst case" considerations, i.e. that calibration interval will be chosen which still ensures a well-timed calibration in the most unfavourable conditions. If instead an indicator is determined which is characteristic of the state of the reagent, the calibration may take place less frequently under favourable conditions without the analytical accuracy suffering as a result.

As mentioned, data on the sample or the analyses, which are stored in the storage means 25, may also be allowed for as system-immanent influencing variables at the initiation of a calibration.

If the system is used for the analysis of a plurality of different kinds of sample (for example serum and urine), data on the sample sequence may be stored and interrogated. In this way it is possible to carry out a re-calibration in good time prior to the analysis of the first sample of a different kind of sample.

Data on the analyses which are stored in the storage means 25 may likewise be of importance for the initiation of a calibration. For example, an additional interrogation may take place prior to each calibration to determine whether the respective parameter has in fact been requested as an analytical value for the samples to be handled in the immediate future. If this is not the case, the calibration may be delayed accordingly. Should such a facility be provided, a detection of specially defined samples, in particular of so-called "emergency samples", should on the other hand be possible, for which either a sample detector with a bar code reader (similar to FIG. 3 and FIG. 4) or an information item stored in the storage means 25 may be used. It is thereby guaranteed that on the interpolation of additional emergency samples into the previously planned sample sequence a re-calibration takes place if a parameter has to be determined whose calibration had been put off initially.

It may also be desirable to take into account, as an influencing variable for the initiation of the calibration, the number of analyses carried out for a particular parameter. This applies in particular if a reagent reacts particularly sensitively to the entrainment of substances out of other reagents and consequently re-calibration is necessary after a particular number of reagent pipettings.

Servicing operations on the analysis system or conversions of the system may be allowed for as system-immanent influencing variables. If the analysis system itself records such operations and stores corresponding information items, an automatic recalibration may be triggered.

In all cases the initiation of the calibration takes place parameter-specifically, i.e. it is adapted individually to the requirements of the respective parameter. It may be expedient for some particular parameters to trigger the calibration on principle as a function of time and to take merely complementary account of other influencing variables, while for other parameters the calibration will be initiated in each case on the basis of one or more indicators characteristic of the state of the reagent.

The means for implementing the described functions during the calibration initation cycle are readily available to the skilled person. If a hardware implementation is desired, logic decisions such as whether or not a calibration should be initiated when the reagent bottle is switched, may be implemented by means of usual logic gates (AND-gates, Or-gates etc. . . . ). The logic value of the calibration influencing variable (e.g. switching of bottle) and control value (e.g. whether or not recalibration or switching of bottle is required) are connected to such gate or gate array in known manner to produce the required response. Where the initiation of the calibration is dependent on the interrogation of a control value which is a numerical quantity (such as a limit value of the optical absorption of the reagent), a comparator circuit (to compare with the control value, e.g. the preset limit value of the optical absorption) would be the standard hardware means for implementing this step of the calibration initiation cycle. In practice, preferably the decisions during the calibration initation cycle are carried out software controlled by correspondingly programming the microprocessor of the processing means of the apparatus.

What is claimed is:

1. A method for a selective automatic analysis of a body fluid for a plurality of parameters, each of said parameters corresponding to an analyte contained in the body fluid, said method comprising the steps of:

providing an apparatus for the selective automatic analysis which includes reaction vessel holding means having a plurality of reaction vessels, liquid reagent holding means having a plurality of reagent vessels holding different reagents for different analyses, calibrator holding means having a plurality of calibrator vessels holding at least one calibrator, test sample holding means having a plurality of test sample vessels holding different test samples, measuring means for measuring a physically detectable measuring quantity from a reaction solution in a selected reaction vessel, processing means for evaluating reactions in all selected reaction vessels and for controlling operation of the apparatus, and calibration control means for controlling automatic parameter-specific predetermined calibrations;

at least one determining step of determining if a calibration is to be initiated based on at least one system-immanent calibration- influencing variable, including storing in a first memory means at least one system-immanent calibration-influencing variable, defining at least one control value for a specific parameter being calibrated and corresponding to the at least one system-immanent calibration-influencing variable, and storing said at least one control value in a second memory means;

automatically initiating a calibration by reacting the at least one calibrator for a selected parameter in a selected reaction vessel with at least one selected reagent so as to produce a reaction when said calibration-influencing variable has a predetermined value in relation to said control value;

measuring the physically detectable measuring quantity resulting from the reaction;

calibrating the apparatus for the selected parameter based on the physically detectable quantity by adjusting an evaluation curve describing a functional relationship of the measured physical quantity and a concentration of the parameter;

performing selected tests for the selected parameter using selected reaction vessels, test samples and reagents;

processing test results of the selected tests so as to output evaluations of the selected tests, said step of processing the test results including a step of calculating the concentration of said parameter by means of said evaluation curve; and displaying the evaluation of the selected tests based on the corrected test results, wherein said at least one determining step of determining if a calibration is to be initiated based on at least one system-immanent calibration-influencing variable includes a first determining step including the steps of detecting a manufacturing batch of the reagent in one of the plurality of reagent vessels, and determining that a recalibration is necessary when it is determined that the manufacturing batch of the reagent is different from a previously detected manufacturing batch, said method further comprising a second determining step of determining if a calibration is to be initiated based upon at least one system immanent calibration influencing variable, said second determining step including the steps of detecting switching of a reagent vessel with another reagent vessel, and storing data on the switching of reagent vessels in the first memory means as a calibration-influencing variable.

2. A method for a selective automatic analysis as recited in claim 1, wherein said step of performing selected tests includes analyzing at least one control solution which is different from the calibrator used for calibrating the apparatus, and which contains a known concentration of an analyte.

3. A method for a selective automatic analysis according to claim 1, wherein said first determining step includes the steps of reading a machine-readable code attached to a reagent vessel which contains manufacturing batch data, and determining if a calibration is to be initiated based upon the data on the machine-readable code attached to the reagent vessels.

4. A method for a selective automatic analysis of a body fluid as recited in claim 1, wherein said at least one determining step includes a step of comparing the system-immanent calibration-influencing variable and the control value, wherein results of said comparing step are used to determine if a calibration is to be initiated.

5. A method for a selective automatic analysis of a body fluid for a plurality of parameters, each of said parameters corresponding to an analyte contained in the body fluid, said method comprising the steps of:

providing an apparatus for the selective automatic analysis which includes reaction vessel holding means having a plurality of reaction vessels, liquid reagent holding means having a plurality of reagent vessels holding different reagents for different analyses, calibrator holding means having a plurality of calibrator vessels holding at least one calibrator, test sampleholding means having a plurality of test sample vessels holding different test samples, measuring means for measuring a physically detectable measuring quantity for a reaction solution in a selected reaction vessel, processing means for evaluating reactions in all selected reaction vessels and for controlling operation of the apparatus, and calibration control means for controlling automatic parameter-specific predetermined calibrations;

at least one determining step of determining if a calibration is to be initiated based on at least one system-immanent calibration- influencing variable, including storing in a first memory means at least one system-immanent calibration-influencing variable, defining at least one control value for a specific parameter being calibrated and corresponding to the at least one system-immanent calibration-influencing variable, and storing said at least one control value in a second memory means;

automatically initiating a calibration by reacting the at least one calibrator for a selected parameter in a selected reaction vessel with at least one selected reagent so as to produce a reaction when said calibration-influencing variable has a predetermining value in relation to said control value;

measuring the physically detectable measuring quantity resulting from the reaction;

calibrating the apparatus for the selected parameter based on the physically detectable quantity by adjusting an evaluation curve describing a functional relationship of the measured physical quantity and a concentration of the parameter;

performing selected tests for the selected parameter using selected reaction vessels, test samples and reagents;

processing test results of the selected tests so as to output evaluations of the selected tests, said step of processing the test results including a step of calculating the concentration of said parameter by means of said evaluation curve; and displaying the evaluation of the selected tests based on the corrected test results, wherein said at least one determining step of determining if a calibration is to be initiated based on at least one system-immanent calibration-influencing variable includes a first determining step including the steps of detecting a manufacturing batch of the reagent in one of the plurality of reagent vessels, and determining that a recalibration is necessary when it is determined that the manufacturing batch of the reagent is different from a previously detected manufacturing batch, said method further comprising a second determining step of determining if a calibration is to be initiated based upon at least one system immanent calibration-influencing variable, said second determining step including the steps of detecting a filling level of the reagent in at least one of the plurality of reagent vessels, and storing data on the filling level for the reagent in said reagent vessel in the first memory means as a calibration-influencing variable.

6. A method for a selective automatic analysis as recited in claim 5, wherein said step of performing selected tests includes analyzing at least one control solution which is different from the calibrator used for calibrating the apparatus, and which contains a known concentration of an analyte.

7. A method for a selective automatic analysis according to claim 5, wherein said first determining step includes the steps of reading a machine-readable code attached to a reagent vessel which contains manufacturing batch data, and determining if a calibration is to be initiated based upon the data on the machine-readable code attached to the reagent vessels.

8. A method for a selective automatic analysis of a body fluid as recited in claim 5, wherein said at least one determining step includes a step of comparing the system-immanent calibration-influencing variable and the control value, wherein results of said comparing step are used to determine if a calibration is to be initiated.

9. A method for a selective automatic analysis of a body fluid for a plurality of parameters, each of said parameters corresponding to an analyte contained in the body fluid, said method comprising the steps of:
providing an apparatus for the selective automatic analysis which includes reaction vessel holding means having a plurality of reaction vessels, liquid reagent holding means having a plurality of reagent vessels holding different reagents for different analyses, calibrator holding means having a plurality of calibrator vessels holding at least one calibrator, test sample holding means having a plurality of test sample vessels holding different test samples, measuring means for measuring a physically detectable measuring quantity from a reaction solution in a selected reaction vessel, processing means for evaluating reactions in all selected reaction vessels and for controlling operation of the apparatus, and calibration control means for controlling automatic parameter-specific predetermined calibrations;
at least one determining step of determining if a calibration is to be initiated based on at least one system-immanent calibration- influencing variable, including storing in a first memory means at least one system-immanent calibration-influencing variable, defining at least one control value for a specific parameter being calibrated and corresponding to the at least one system-immanent calibration-influencing variable, and storing said at least one control value in a second memory means;
automatically initiating a calibration by reacting the at least one calibrator for a selected parameter in a selected reaction vessel with at least one selected reagent so as to produce a reaction when said calibration-influencing variable has a predetermined value in relation to said control value;
measuring the physically detectable measuring quantity resulting from the reaction;
calibrating the apparatus for the selected parameter based on the physically detectable quantity by adjusting an evaluation curve describing a functional relationship of the measured physical quantity and a concentration of the parameter;
performing selected tests for the selected parameter using selected reaction vessels, test samples and reagents;

processing test results of the selected tests so as to output evaluations of the selected tests, said step of processing the test results including a step of calculating the concentration of said parameter by means of said evaluation curve; and
displaying the evaluation of the selected tests based on the corrected test results,
wherein said at least one determining step of determining if a calibration is to be initiated based on at least one system-immanent calibration-influencing variable includes a first determining step including the steps of detecting a manufacturing batch of the reagent in one of the plurality of reagent vessels, and determining that a recalibration is necessary when it is determined that the manufacturing batch of the reagent is different form a previously detected manufacturing batch, said method further comprising
a second determining step of determining if a calibration is to be initiated based upon at least one system-immanent calibration-influencing variable, said second determining step including the steps of determining an optical absorption of the pure reagent without any sample added thereto in at least one of the plurality of reagent vessels, and storing data on the optical absorption for the reagent in the at least one reagent vessel in the first memory means as a calibration-influencing variable.

10. A method for a selective automatic analysis as recited in claim 9, wherein said step of performing selected tests includes analyzing at least one control solution which is different from the calibrator used for calibrating the apparatus, and which contains a known concentration of an analyte.

11. A method for a selective automatic analysis according to claim 9, wherein said first determining step includes the steps of reading a machine-readable code attached to a reagent vessel which contains manufacturing batch data, and determining if a calibration is to be initiated based upon the data on the machine-readable code attached to the reagent vessels.

12. A method for a selective automatic analysis of a body fluid as recited in claim 9, wherein said at least one determining step includes a step of comparing the system-immanent calibration-influencing variable and the control value, wherein results of said comparing step are used to determine if a calibration is to be initiated.

13. A method for a selective automatic analysis of a body fluid for a plurality of parameters, each of said parameters corresponding to an analyte contained in the body fluid, said method comprising the steps of:
providing an apparatus for the selective automated analysis which includes reaction vessel holding means having a plurality of reaction vessels, liquid reagent holding means having a plurality of reagent vessels holding different reagents for different analyses, calibrator holding means having a plurality of calibrator vessels holding at least one calibrator, test sample holding means having a plurality of test sample vessels holding different test samples, measuring means for measuring a physically detectable measuring quantity from a reaction solution in a selected reaction vessel, processing means for evaluating reactions in all selected reaction vessels and for controlling operation of the apparatus, and calibration control means for controlling automatic parameter-specific predetermined calibrations;

at least one determining step of determining if a calibration is to be initiated based on at least one system-immanent calibration- influencing variable, including storing in a first memory means at least one system-immanent calibration-influencing variable, defining at least one control value for a specific parameter being calibrated and corresponding to the at least one system-immanent calibration-influencing variable, and storing said at least one control value in a second memory means;

automatically initiating a calibration by reacting the at least one calibrator for a selected parameter in a selected reaction vessel with at least one selected reagent so as to produce a reaction when said calibration-influencing variable has a predetermined value in relation to said control value;

measuring the physically detectable measuring quantity resulting from the reaction;

calibrating the apparatus for the selected parameter based on the physically detectable quantity by adjusting an evaluation curve describing a functional relationship of the measured physical quantity and a concentration of the parameter;

performing selected tests for the selected parameter using selected reaction vessels, test samples and reagents;

processing test results of the selected tests so as to output evaluations of the selected tests, said step of processing the test results including a step of calculating the concentration of said parameter by means of said evaluation curve; and displaying the evaluation of the selected tests based on the corrected test results, wherein said at least one determining step of determining if a calibration is to be initiated based on at least one system-immanent calibration-influencing variable includes a first determining step including the steps of detecting a manufacturing batch of the reagent in one of the plurality of reagent vessels, and determining that a recalibration is necessary when it is determined that the manufacturing batch of the reagent is different from a previously detected manufacturing batch, said method further comprising a second determining step of determining if a calibration is to be initiated based upon at least one system immanent calibration-influencing variable, said second determining step including the steps of determining a pH value of the pure reagent having no test sample added thereto in at least one of the plurality of reagent vessels, and storing data on the pH value for the reagent in said at least one of the plurality of reagent vessels in the first memory means as a calibration-influencing variable.

14. A method for a selective automatic analysis as recited in claim 13, wherein said step of performing selected tests includes analyzing at least one control solution which is different from the calibrator used for calibrating the apparatus, and which contains a known concentration of an analyte.

15. A method for a selective automatic analysis according to claim 13, wherein said first determining step includes the steps of reading a machine-readable code attached to a reagent vessel which contains manufacturing batch data, and determining if a calibration is to be initiated based upon the data on the machine-readable code attached to the reagent vessels.

16. A method for a selective automatic analysis of a body fluid as recited in claim 13, wherein said at least one determining step includes a step of comparing the system-immanent calibration-influencing variable and the control value, wherein results of said comparing step are used to determine if a calibration is to be initiated.

17. An analysis system for the selective automatic analysis of a body fluid for a plurality of parameters, each of said parameters corresponding to an analyte contained in the body fluid, comprising:

reaction vessel holding means having seats for a plurality of reaction vessels, for holding the reaction vessels;

liquid reagent holding means having seats for a plurality of reagent vessels, for holding the reagent vessels, said plurality of reagent vessels holding different reagents for different analyses;

calibrator holding means having seats for a plurality of calibrator vessels, for holding at least one calibrator in the plurality of calibrator vessels, the calibrator containing an analyte in a known concentration;

test sample holding means having seats for a plurality of test sample vessels, for holding the test sample vessels, said plurality of test sample vessels holding different test samples;

pipetting transfer means for transferring a calibrator from a selected calibrator vessel, a test sample from a selected test sample vessel and at least one reagent from at least one of the plurality of reagent vessels to a selected reaction vessel in said reaction vessel holding means;

measuring means operatively connected with said reaction vessel holding means for measuring a physically detectable measuring quantity from a reaction solution contained in a selected reaction vessel;

processing means connected to said measuring means, for evaluating reactions in selected reaction vessels and displaying a result of the reactions, and for controlling the operations of the system; and calibration control means connected to said processing means, for automatically initiating individual calibrations of the parameters of said analysis system, said calibration control means including determining means for determining at least one system immanent calibration-influencing variable, first memory means for storing data on the at least one system immanent calibration-influencing variable, second memory means for storing a control value defined for a specific parameter, said first memory means and said second memory means being connected to a calibration determining means for determining whether to initiate a calibration for said parameter based on said at least one stored system immanent calibration-influencing variable and said control value and for initiating the calibration for said parameter, wherein the first memory means further stores, as calibration-influencing variables, data on at least one of the type, number, and sequence of the test samples to be analyzed.

18. A method for a selective automatic analysis of a body fluid for a plurality of parameters, each of said parameters corresponding to an analyte contained in the body fluid, said method comprising the steps of:

providing an apparatus for the selective automatic analysis which includes reaction vessel holding means having a plurality of reaction vessels, liquid reagent holding means having a plurality of reagent vessels holding different reagents for different analyses, calibrator holding means having a plurality of calibrator vessels holding at least one calibrator, test sample holding means having a plurality of test sample vessels holding different test samples, measuring means for measuring a physically detectable measuring quantity from a reaction solution in a selected reaction vessel, processing means for evaluating reactions in all selected reaction vessels and for controlling operation of the apparatus, and calibration control means for controlling automatic parameter-specific predetermined calibrations;

at least one determining step of determining if a calibration is to be initiated based on at least one system-immanent calibration-influencing variable, storing in a first memory means at least one system immanent calibration-influencing variable, defining at least one control value for a specific parameter being calibrated and corresponding to the at least one system immanent calibration-influencing variable, and storing said at least one control value in a second memory means;

automatically initiating a calibration by reacting the at least one calibrator for a selected parameter in a selected reaction vessel with at least one selected reagent so as to produce a reaction when said calibration-influencing variable has a predetermined value in relation to said control value;

measuring the physically detectable measuring quantity resulting from the reaction;

calibrating the apparatus for the selected parameter based on the physically detectable quantity by adjusting an evaluation curve describing a functional relationship of the measured physical quantity and a concentration of the parameter;

performing selected tests for the selected parameter using selected reaction vessels, test samples and reagents;

processing test results of the selected tests so as to output evaluations of the selected tests, said step of processing the test results including a step of calculating the concentration of said parameter by means of said evaluation curve; and displaying the evaluation of the selected tests based on the corrected test results, wherein said at least one step of determining if a calibration is to be initiated based on at least one system-immanent calibration-influencing variable includes a first determining step including the step of storing, as calibration-influencing variables, data on at least one of the type, number and sequence of the test samples to be analyzed.

19. A method for a selective automatic analysis of a body fluid as recited in claim 18, wherein said at least one determining step includes a step of comparing the system-immanent calibration-influencing variable and the control value, wherein results of said comparing step are used to determine if a calibration is to be initiated.

20. A method for a selective automatic analysis according to claim 18, wherein said first determining step includes the steps of reading a machine-readable code attached to a reagent vessel which contains manufacturing batch data, and determining if a calibration is to be initiated based upon the data on the machine-readable code attached to the reagent vessels.

21. A method for a selective automatic analysis of a body fluid as recited in claim 18, wherein said at least one determining step includes a step of comparing the system-immanent calibration-influencing variable and the control value, wherein results of said comparing step are used to determine if a calibration is to be initiated.

* * * * *